United States Patent
Saito et al.

(10) Patent No.: US 6,766,046 B1
(45) Date of Patent: Jul. 20, 2004

(54) PLATE GLASS SHATTER TESTING METHOD, DEVICE, IMAGING METHOD FOR GLASS TESTING AND IMAGE SIGNAL PROCESSING METHOD

(75) Inventors: Hitoshi Saito, Sapporo (JP); Tetsuo Tajima, Chita-gun (JP)

(73) Assignees: Asahi Glass Company Ltd., Tokyo (JP); Nippon Control System Corporation, Tokyo (JP)

( * ) Notice: Subject to any disclaimer, the term of this patent is extended or adjusted under 35 U.S.C. 154(b) by 0 days.

(21) Appl. No.: 09/403,023
(22) PCT Filed: Feb. 18, 1999
(86) PCT No.: PCT/JP99/00698
 § 371 (c)(1),
 (2), (4) Date: Dec. 29, 1999
(87) PCT Pub. No.: WO99/42807
 PCT Pub. Date: Aug. 26, 1999

(30) Foreign Application Priority Data

Feb. 19, 1998 (JP) .......................................... 10-037679

(51) Int. Cl.[7] ................................................ G06K 9/00
(52) U.S. Cl. ...................................................... 382/141
(58) Field of Search ................................ 382/141, 143; 356/237.1, 239.1, 239.3, 239.7, 432; 348/86, 92, 125, 127, 128

(56) References Cited

U.S. PATENT DOCUMENTS

| | | | |
|---|---|---|---|
| 3,721,501 A | * | 3/1973 | Atkinson et al. ........... 356/432 |
| 4,662,926 A | | 5/1987 | Aratani et al. |
| 4,908,875 A | | 3/1990 | Assael et al. |
| 5,016,099 A | | 5/1991 | Bongardt et al. |
| 5,146,282 A | | 9/1992 | Guering et al. |
| 5,471,297 A | | 11/1995 | Tani |
| 5,768,412 A | | 6/1998 | Mitsuyama et al. |
| 6,208,412 B1 | * | 3/2001 | Ladewski ................ 356/239.1 |

FOREIGN PATENT DOCUMENTS

| | | |
|---|---|---|
| EP | 0 712 094 | 5/1996 |
| EP | 0 781 730 | 7/1997 |
| JP | 51-47278 | 10/1974 |
| JP | 51-47278 | 4/1976 |
| JP | 8-145871 | 6/1996 |

OTHER PUBLICATIONS

G. G. Gordon, Proceedings SPIE, vol. 2665, pp. 244–252, "Automated Glass Fragmentation Analysis", Jan. 31, 1996.
J. Haywood, et al., Glass Processing Days, pp. 366–370, "Automated Counting System for the ECE Fragmentation Test", Sep. 13–15, 1997.
Glass Processing Days; 13–15; Sep. 97; "Automated Counting System for the ECE Fragmentation Test"; Ford Motor Co; J. Haywood, et al. (pp. 366–370).

* cited by examiner

Primary Examiner—Vikkram Bali
(74) Attorney, Agent, or Firm—Oblon, Spivak, McClelland, Maier & Neustadt, P.C.

(57) ABSTRACT

A sheet screen is provided on one of sides of test glass, and a projected image of the test glass is electronically and directly picked up. After tone image signals of the test glass thus picked up are binarized while modifying threshold values according to brightness of a background in the tone image, the number of fragments, the area of the greatest fragment and the length of the longest fragment are calculated. Thus, operations, such as calculating the number of the fragments, can be automatically performed by directly picking up an image of the test glass, allowing a fragmentation test to be carried out with good operability and high precision.

11 Claims, 11 Drawing Sheets

Tentacles for tone distribution detection

PLATE GLASS SHATTER TESTING METHOD, DEVICE, IMAGING METHOD FOR GLASS TESTING AND IMAGE SIGNAL PROCESSING METHOD

BACKGROUND OF THE INVENTION

1. Technical Field

The present invention relates to plate-shaped glass fragmentation testing method and device, image pickup method for glass test, and image signal processing method, which are used for quality assurance in the production of plate glass.

2. Background Art

Most of windowpanes for automobiles and so on are made of tempered glass, which has had compressive stress applied to surfaces thereof to improve resistance to tensile stress. In the production of such a kind of plate-shaped glass, a fragmentation test or a similar test has been carried out as a quality assurance test.

The fragmentation test for tempered glass is prescribed in JIS standard (JIS R 3212-1992), ECE standard (E6) or another standard. The fragmentation test is a test wherein test glass is fragmented by applying an impact shock to a certain portion thereof with a punch, the number of fragments in a region with the coarsest fragment included and in a region with the finest fragment included are calculated, and the area of the greatest fragment and the length of the longest fragment in that region are measured to see whether the test glass meets desired specifications, or not.

For the calculation of the fragments or another purpose, a measuring method has been adopted wherein the image of fragmented test glass is exposed to photosensitive paper to obtain an image as a blueprint (hereinbelow, referred to as a blueprinted image), and the measurement is conducted utilizing the blueprinted image. In the measuring method, all operations including the setting of selected regions and the calculation of the number of the fragments have been manually carried out based on the blueprinted image. The conventional measuring method has required considerable labor in the calculating operation for counting the number of the fragments and another operation.

As an example of systems to improve the operability in the fragmentation test, "Automated calculating system for the ECE fragmentation test" Ford Motor Co. (GLASS PROCESSING DAYS, 13–15, Sep. 1997) discloses a technique that the calculating operation for counting the number of the fragments and another operation in the blueprinted image are automatically carried out by a computer. According to this automated calculating technique, there is no need for an operator to manually count the number of the fragments, reducing the number of the steps required for the calculating operation.

Since the measurement of the number of the fragments and another operation have been manually made by an operator in the conventional manual measuring method for the fragmentation test as spreaded area, the conventional manual measuring method has created a problem in that the calculating operation in the fragmentation test requires many steps and much labor cost.

On the other hand, the automated calculating technique stated above can reduce the number of the required steps in comparison with the manual calculating operation. However, the automated calculating technique requires a step to prepare a blueprinted image and a step to take a picture of the blueprinted image since the automated calculating technique has carried out the measurement using the blueprinted image as in the conventional manual measuring method.

The present invention has been proposed from this viewpoint, and the present invention has an object to provide a plate glass fragmentation testing method and device, an imaging method for glass test, and an image signal processing method capable of directly picking up an image of test glass and dealing with a calculating operation of the number of fragments and another operation in automated fashion thereby to carry out a fragmentation test with good operability and high precision.

The present invention provides a plate-shaped glass fragmentation testing method characterized in that the method comprises a glass image pickup step for providing a sheet screen in substantially close contact with one of sides of plate-shaped test glass, fragmenting the test glass, and irradiating light for image pickup to the other side of the test glass to electronically and directly pick up a projected image of the fragmented test glass from the side of the test glass with the screen provided; and an image processing step for performing a calculating operation to calculate the number of fragments of the test glass, the area of the greatest fragment and the length of the longest fragment in at least a selected region based on tone image signals of the test glass thus obtained.

By directly picking up the test glass according to this method, a clear tone image can be provided, and operations, such as calculating the number of the fragments, can be automatically performed based on the tone image signals, allowing a fragmentation test to be carried out with good operability and high precision.

It is preferable that in the image processing step, a binarizing operation is performed to binarize the tone image signals of the test glass while modifying threshold values according to brightness of a background in the tone image, and the calculating operation is performed based on the binarized image signals after the binarization.

It is further preferable that in the binarization, the tone image of the fragmented portions with a cracked portion of the glass eliminated is used as a threshold value distribution image for binarization, and the binarization of the tone image signals is performed according to the brightness of the background based on the threshold value distribution image.

The present invention also provides a plate glass fragmentation testing method characterized in that the method comprises a glass image pickup step for electronically and directly picking up plate-shaped test glass in fragmented fashion, a binarizing step for binarizing tone image signals of the test glass thus obtained while modifying threshold values according to brightness of a background in the tone image, and a calculating step for calculating the number of fragments of the test glass, the area of the greatest fragment and the length of the longest fragment in at least a selected region based on the binarized image signals after the binarization.

By this method, the tone image signals can be binarized in optimum fashion according to brightness of a background in the tone image obtained by directly picking up the test glass, and operations, such as calculating the number of the fragments, can be automatically performed based on the binarized image signals, allowing a fragmentation test to be carried out with good operability and high precision.

It is preferable that in the glass image pickup step, a sheet screen is provided on one of sides of the test glass in substantially close contact, and light for image pickup is irradiated to the other side of the test glass to pick up a projected image of the test glass from the side of the test glass with the screen provided.

More preferably, the plate-shaped glass fragmentation testing method further comprises a display step for displaying at least the tone image of the test glass and results of the calculating operation.

It is preferable that the plate-shaped glass fragmentation testing method further comprises a storage step for storing at least data of the tone image of the test glass and data of the results of the calculating operation on a recording medium in correlated fashion.

The present invention also provides a plate-shaped glass fragmentation testing device characterized in that the device comprises an image pickup unit including a light source to producing light for image pickup to irradiate fragmented plate-shaped test glass from one of sides thereof, a sheet screen provided on the side of the test glass remote from the light source in substantially close contact, and an image pickup means for electronically and directly picking up a projected image of the test glass from the side of the test glass with the screen provided; and an image processing unit including a calculating means for calculating the number of fragments of the test glass, the area of the greatest fragment and the length of the longest fragment in at least a selected region based on tone image signals of the test glass thus obtained.

By directly picking up the test glass according to this arrangement, a clear tone image can be provided, and operations, such as calculating the number of the fragments, can be automatically performed based on the tone image signals, allowing a fragmentation test to be carried out with good operability and high precision.

It is preferable that the image processing unit includes a binarizing means for binarizing the tone image signals of the test glass while modifying threshold values according to brightness of a background in the tone image, and the calculating means performs the calculation based on the binarized image signals after the binarization.

It is further preferable that the binarizing means utilizes the tone image of the fragmented portions with a cracked portion of the glass eliminated as a threshold value distribution image for binarization, and the binarization of the tone image signals is performed according to the brightness of the background based on the threshold value distribution image.

The present invention also provides a plate-shaped glass fragmentation testing device characterized in that the device comprises an image pickup means for electronically and directly picking up plate-shaped test glass in fragmented fashion, a binarizing means for binarizing tone image signals of the test glass thus obtained while modifying threshold values according to brightness of a background in the tone image, and a calculating means for calculating the number of fragments of the test glass, the area of the greatest fragment and the length of the longest fragment in at least a selected region based on the binarized image signals after the binarization.

By this arrangement, the tone image signals can be binarized in optimum fashion according to the brightness of the background in the tone image obtained by directly picking up the test glass, and operations, such as calculating the number of the fragments, can be automatically performed based on the binarized image signals, allowing a fragmentation test to be carried out with good operability and high precision.

More preferably, the plate-shaped glass fragmentation testing device further comprises a display means for displaying at least the tone image of the test glass and results of the calculation.

It is preferable that the plate glass fragmentation testing device further comprises storage for storing at least data of the tone image of the test glass and data of the results of the calculation on a recording medium in correlated fashion.

The present invention also provides an image pickup method for glass fragmentation test characterized in that the method comprises a step for providing a sheet screen in substantially close contact with one of sides of test glass, a step for irradiating light for image pickup to the other side of the test glass, and a step for electronically and directly picking up a projected image of the test glass from the side of the test glass with the screen provided.

The present invention also provides an image signal processing method for glass fragmentation test characterized in that the method comprises a step for inputting tone image signals obtained by picking up test glass, a binarizing step for binarizing the tone image signals of the test glass thus obtained while modifying threshold values according to brightness of a background in the tone image, and a calculating step for calculating the number of fragments of the test glass, the area of the greatest fragment and the length of the longest fragment in at least a selected region based on the binarized image signals after the binarization.

It is preferable that the binarizing step of the image signal processing method for glass fragmentation test includes a first binarizing step for binarizing the tone image signals into cracked portions and fragmented portions based on a threshold value image obtained by modifying threshold values according to brightness of a background in the tone image, a second binarizing step for examining a tone distribution in a plurality of directions in a certain region around a noteworthy pixel of the tone image and for performing binarization so as to recognize the noteworthy pixel as a cracked portion when in at least one direction of the tone distribution, a central portion is dark and both end portions are bright, and a binarized image combining step for combining the image signals binarized in the first binarizing step and the image signals binarized in the second binarizing step. Such binarization may be applied to the plate-shaped glass fragmentation testing methods, the plate-shaped glass fragmentation testing devices or another one.

By this binarization, the first binarizing step based on a threshold value image obtained by threshold values according to brightness of the background in the tone image, and the second binarizing step based on the minute tone distribution in the plurality of direction in the certain region around the noteworthy pixel can be performed, and the results of both binarization can be combined to binarize the tone image signals in more optimum fashion, obtaining the binarized image signals in an effective way without failing detection of a cracked portion. As a result, operations, such as calculating the fragments, can be performed more accurately, and the fragmentation test can be carried out with high precision.

BRIEF DESCRIPTION OF THE DRAWINGS

FIG. 11 is a schematic view showing a criterion for giving recognition as a cracked portion when the binarizing operation is carried out based on the minute tone distribution.

BEST MODE FOR CARRYING OUT THE INVENTION

Now, embodiments according to the present invention will be described in reference to the drawings.

Figure 1:
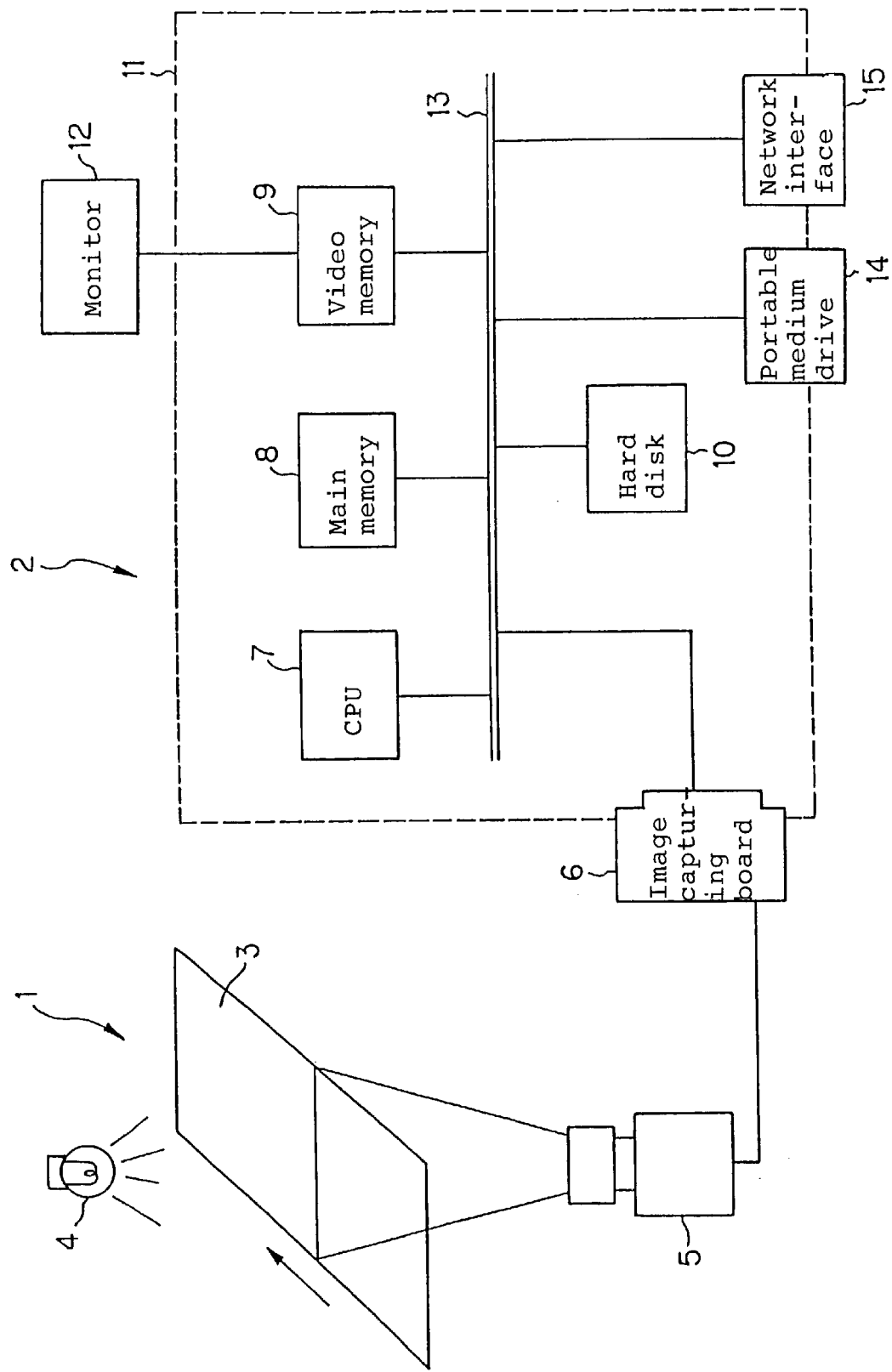
FIG. 1 is a block diagram showing an example of the structure of the plate-shaped glass fragmentation testing device according to an embodiment of the present invention.

First, the structure of the plate-shaped glass fragmentation testing device according to an embodiment of the present invention will be described referring to FIG. 1. The fragmentation testing device is a device that carries out a fragmentation test to find the number of fragments at a certain position, the area of the greatest fragment, the length of the longest fragment and another factor with respect to plate-shaped glass fragmented according to a standard, such as JIS R 3212-1992. The fragmentation testing device is configured to include an image pickup unit 1 for picking up an image of fragmented test glass, and an image processing unit 2 for receiving the image data of the test glass obtained by the image pickup unit 1 and performing operations such as, calculating of the number of the fragments, and finding the area of the greatest fragment and the length of the longest fragment.

The image pickup unit 1 is configured to include a light source 4 for irradiating light for image pickup toward test glass 3, and a camera 5 for picking up an image of the test glass 3. The camera 5 is configured to include an image pickup element, such as a line sensor, wherein an optical image is photoelectrically converted line by line. With the test glass 3 linearly moved in a direction perpendicular to an image pickup line of the line sensor (the direction indicated by the arrow in this figure) by a driver, such as an electric motor, not shown, the camera can pick up the test glass to obtain a two-dimensional tone image of a glass surface.

The image processing unit 2 is configured to include an image signal processing device 11, such as a personal computer, and a monitor 12, such as a CRT. The image signal processing device 11 has an image capturing board 6 mounted thereon to receive image signals outputted from the camera 5 and to convert the image signals into digital signals, and includes a CPU 7, a main memory 8, a video memory 9 and a hard disk 19. The monitor 12 is connected to the image signal processing device 11 to display results obtained by the operations, such as an image of the test glass and the counted number of fragments.

The image capturing board 6, the CPU 7, the main memory 8, the video memory 9 and the hard disk 10 in the image signal processing device 11 are connected together through a bus line 13 to interchange image data, data of a calculating operation and other data. The image signal processing device 11 includes a portable medium drive 14 for recording and reproducing data by putting removable medium, such as a magnet-optical disk, an optical disk, a bulk magnetic disk and a floppy disk, into the drive, and a network interface 15 for interchanging data by connection with an external processing device, an external storage device, an external display device and so on. The image signal processing device 11 may have a detachable hard disk drive or a detachable portable medium drive connected thereto to record image data or other data.

Figure 2:
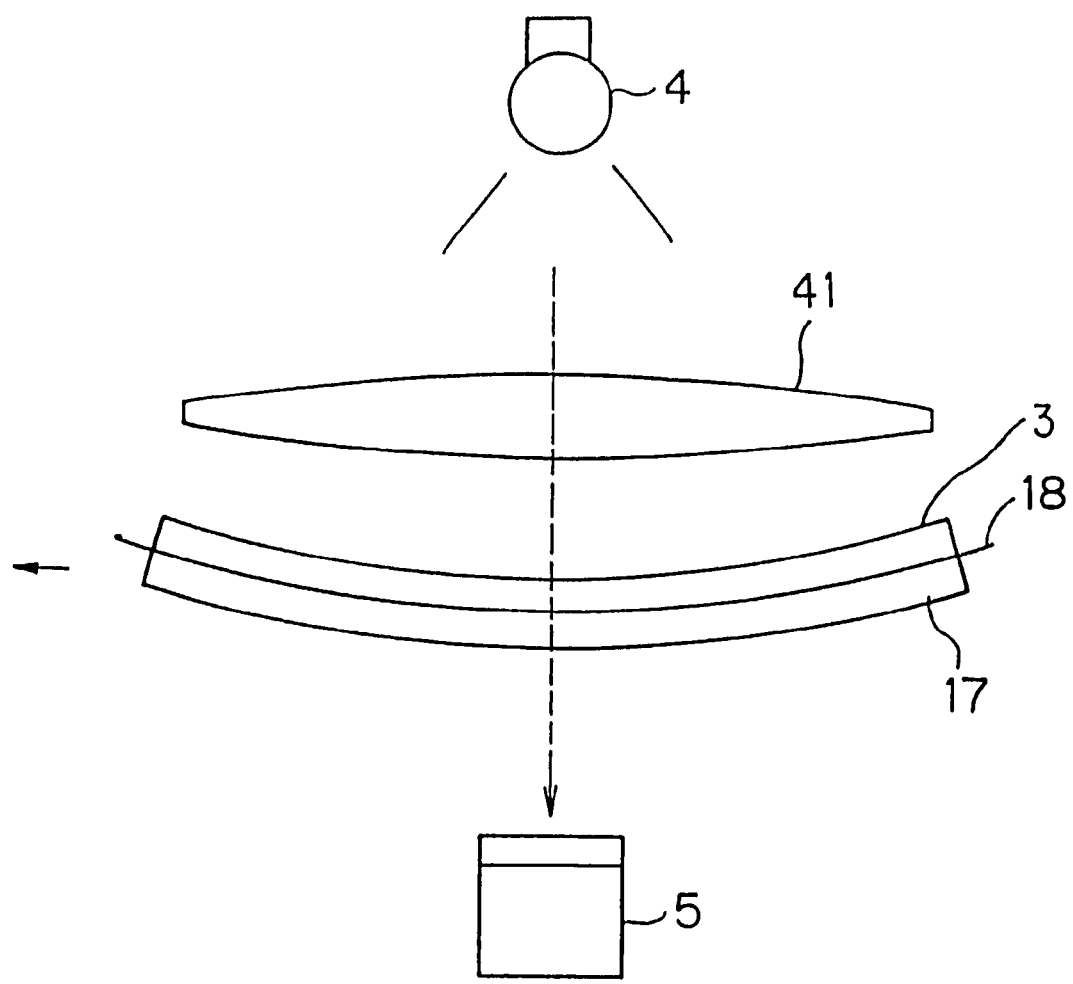
FIG. 2 is a schematic view showing the details of an example of the structure of an image pickup unit.

In FIG. 2 is schematically shown the details of an example of the structure of the image pickup unit 1. In the image pickup unit 1, the test glass 3 is provided between the light source 4 and the camera 5. At the time, a transparent underlying glass sheet 17 as a guide member for putting the test glass 3 thereon, and a screen 18 made of paper or another material for projecting a transmitted image of the glass sheet 3 thereon are provided, and the underlying glass sheet 17, the screen 18 and the test glass 3 are put one another in this order as viewed from the side of the camera as shown in FIG. 2. When picking up an image is carried out with the test glass 3 in close contact with the screen 18, the image produced by light irradiated from the light source 4 and having transmitted through the test glass 3 is projected on the screen 18, and the projected image is picked up by the camera 5.

Between the light source 4 and the test glass 3 may be provided a condensing lens 41, such as a Fresnel lens with grooves formed in concentric fashion thereon, and a convex lens. For example, the condensing lens is provided so that the light source 4 is located at a position close to the focal position of the condensing lens 41. By the addition of an optical element having such a condensing function, the light rays from the light source 4 as a point source can be modified in substantially parallel fashion so as to irradiate the test glass 3 at a small angle of incidences. When the condensing lens 41 is not provided, a small fragment can be merged in the shadow of a crack at a peripheral portion of the projected image so as to be prevented from being seen in some cases since an increase in the angle of incidence of the light rays at the peripheral portion of the test glass 3 shows the crack at the peripheral portion in wider fashion. This phenomenon is particularly noticeable when the test glass 3 is thick. The provision of the condensing lens 41 as stated earlier can show a crack in the projected image of the test glass 3 in sharper fashion and provide an image with tone or cracks shown more uniformly in the entirety. In addition, the image pickup unit 1 can be formed in a small size since the distance between the light source 4 and the test glass 3 can be shortened.

Figure 3:
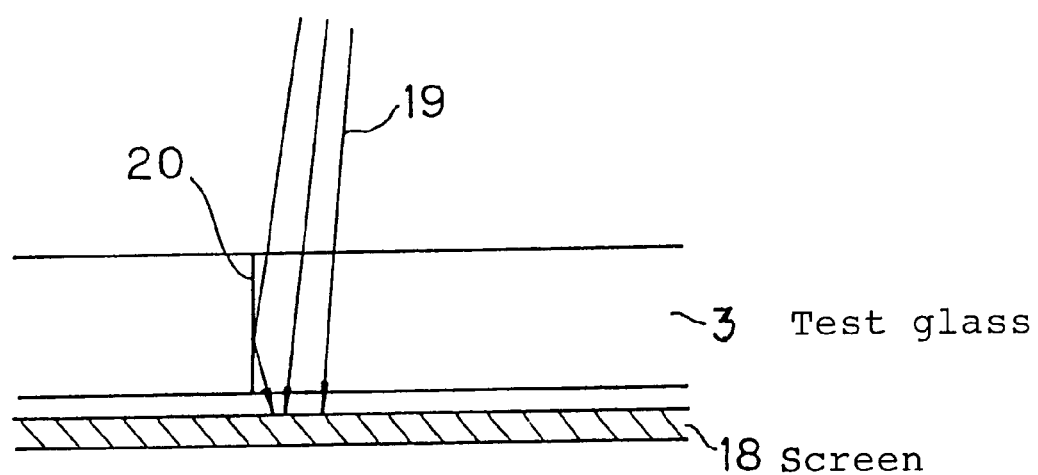
FIG. 3 is a schematic view showing rays of illuminating light transmitting through test glass.

When the fragmented test glass 3 is picked up, the light rays 19 from the light source 4 enter the screen 18 through the test glass 3 as shown in FIG. 3. At a crack 20, the light rays 19 arrive at the screen 18, being scattered or reflected by a surface of the crack 20. As a result, an amount of light that arrives at a portion just under the crack is decreased by the scatter of light rays to produce a dark shadow on the screen 18. On the other hand, an amount of light is increased to produce a light portion at a location close to the crack on the screen 18 since the light rays subjected to total defection on the surface of the crack are added to transmitted light rays. Thus, cracks can have high contrast to provide the tone image of the fragments with a stereoscopic effect.

According to this image pickup method, a portion of a fragment of the test glass 3 without a crack are picked up as a bright surface, and the shadow of a crack is projected on the screen 18 and is picked up as a dark line. As a result, even a crack that is formed substantially perpendicular to the glass surface in a circumferential direction with respect to the impact shock point for fragmentation and that is difficult to be detected by the naked eye can be picked up without failing detection.

The pickup unit 1 is not limited to the arrangement wherein picking up by using the light source 4 and the camera 5 in stationary fashion is carried out with the test glass 3 being moved as in the example, and may be applied to an arrangement that picking up is carried out with the test glass 3 being fixed and the camera 5 being moved. The camera 5 is not limited to one including a line sensor, and may be, e.g., one that includes an image pickup element, such as a CCD, which can pick up a two-dimensional image. The light source 4 is preferable to have directivity and may be a single or a plurality of incandescent lamps, halogen lamps or other lamps.

By the way, the amount of transmitted light varies depending on the thickness, the color or other factors of the test glass 3. The amount of light fed by the light source 4 is required to be varied in order to obtain a projected image with certain brightness. From this viewpoint, it is preferable that a photometer is provided with the camera 5, for instance, to measure the transmittance of the light of the test glass 3 by detecting luminous intensity at the image pickup unit, and the power source voltage for feeding power to the light source 4 is modified according to detected values to control the amount of light fed from the light source. Thus, the effect of the kind and the thickness of the test glass 3 on the projected image can be absorbed to produce an image with certain desired brightness. In this case, a proper amount of light can be ensured without changing the distance between the test glass 3 and the light source 4, and controlling and adjusting the amount of the irradiated light becomes possible.

Next, the fragmentation testing procedures by the fragmentation testing device according to this embodiment and the operation of the device will be explained. As an example, explanation will be made with respect to a case wherein tempered glass having a thickness of 3.5 mm for automobile windowpanes and other purpose is a test object.

At first, the test glass 3 is put on the underlying glass sheet 17 with the screen 18 put thereon, and an impact shock is applied to a certain position of the test glass 3 with a punch or another member. Then, the fragmented test glass 3 is provided in the image pickup unit 1, and the image of the test glass 3 illuminated by the light source 4 is picked up by the camera 5 to obtain tone image signals of the fragmented test glass 3. The pickup is carried out at latest within a period of 3 minutes after fragmentation. For example, when an image pickup element having 5000 pixels per a line (the size of a pixel is ¼ mm) is used as the line sensor of the camera 5 to scan and pick up the test glass 3 in two-dimensional fashion with the test glass being linearly moved, tone image signals having, e.g., 4400×6400 pixels and 256 graduations. The tone image signals are transmitted to the image processing unit 2 through a connecting cable.

Next, the tone image signals are converted into digital data by the image signal processing device 11, image signal processing, such as binarization and calculation, stated later is performed, and information on calculation results of the number of fragments and other data are outputted on the monitor 12 for display in the image processing unit 2. In the image processing unit, the data of the tone image of the picked test glass and the data of the calculation results of the number of the fragments or other data are transmitted to the hard disk 10 or the portable medium drive 14 in correlated fashion to be stored on a recording medium, or are transmitted to an external device in correlated fashion to the network interface 15 for storage, display or other purpose.

In the procedures, the tone image signals transmitted from the camera 5 in the image pickup unit 1 are converted into digital data of the tone image by the image capturing board 6 and are taken into the image signal processing device 11. Under the control of the CPU 7, the digital data of the tone image are stored on the hard disk 10, and the digital data of the tone image are also inputted into the main memory 8 to carry out image signal processing. Data with respect to the tone image for the processing, a processed image and the like are converted into video signal data for display on the monitor and are saved on the video memory 9, and the data are outputted to the monitor 12 for display under the control of the CPU 7.

The image signal processing performed by the image signal processing device 11 will be explained, referring to FIGS. 4–8.

The CPU 7 inputs an image signal processing program stored on the hard disk 10, a ROM not shown or another device into the main memory 8, and carries out the processing operation in accordance with the image signal processing program. The image signal processing program works to perform a calculating region setting function to indicate a set picture for setting a region where operations, such as calculating the number of fragments, are carried out (hereinbelow, referred to as the selected region for calculating fragments), and a calculating function for fragments to calculate the number of the fragments, the area of the greatest fragment, the length of the longest fragment and another factor in the selected region for calculating fragment.

Figure 4:
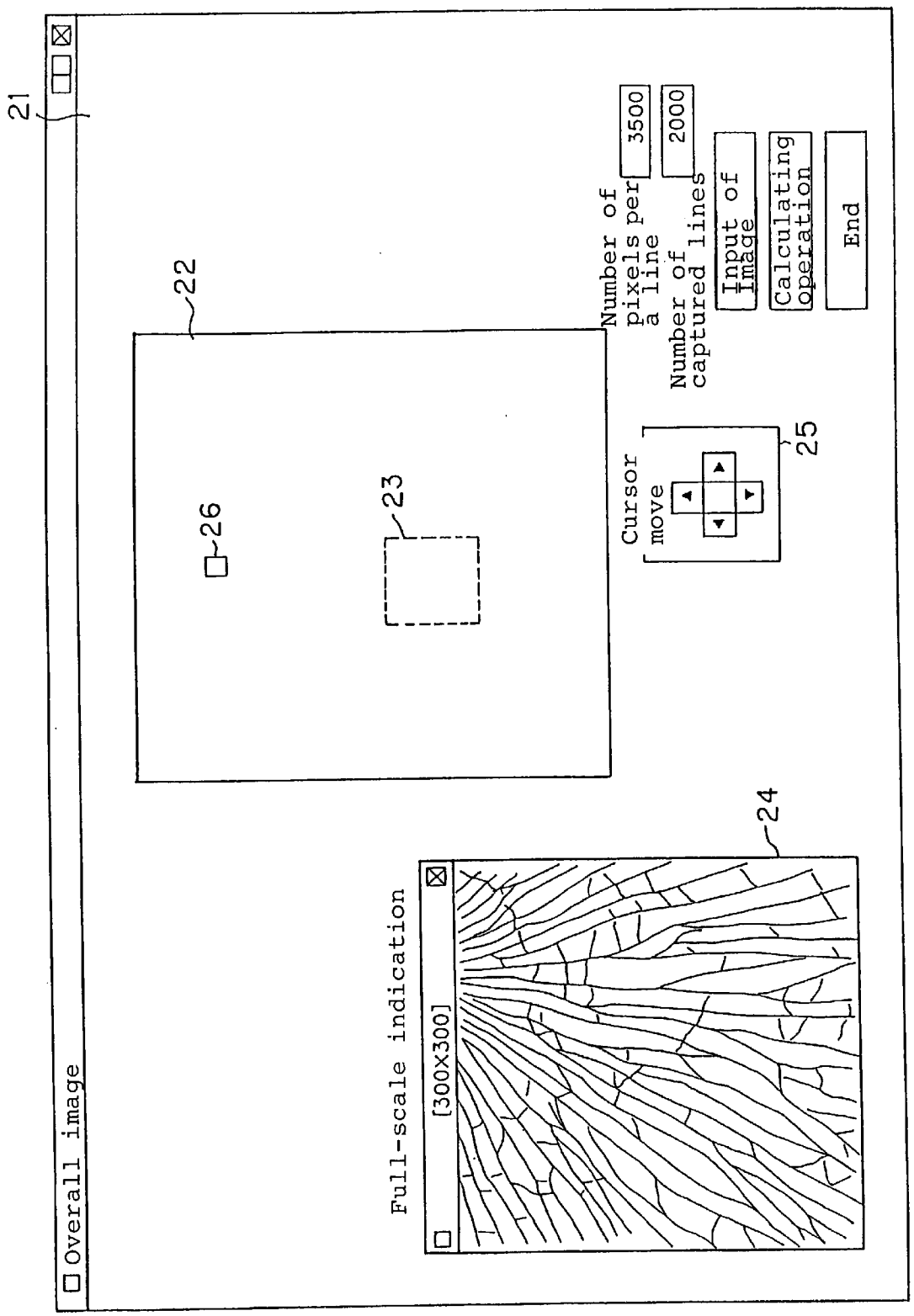
FIG. 4 is a schematic view showing an overall image screen with a picked tone image of the test glass displayed.

First, the overall image screen 21 shown in FIG. 4 is displayed on the monitor 12 to show the tone image of the test glass 3 picked up by the image pickup unit 1 based on the tone image data captured through the image capturing board 6 at a first stage (rough positional designation) of the calculating region setting function. A user carries out the rough designation of the selected region for calculating fragments through this overall image screen 21.

The overall image screen 21 displays a fully indicated image 22 with the outline of the entire test glass 3 shown in reduction and a detailed indication cursor 23 for showing a region to carry out detailed indication at a central portion thereof, and displays a detailed indicated image 24 to show the details of the region specified by the detailed indication cursor 23. The detailed indicated image 24 is shown at a window different from the fully indicated image 22 or shown in parallel and in close proximity to the fully indicated image 22 in the same window so as to be constantly indicated in front. Although the detailed indicated image 24 is a full-scale indicated image (300×300 pixels) in this example, the detailed indicated image may be shown on a scale of ½, ¼ or another value besides a full-scale. The detailed indication cursor 23 can be arbitrarily moved on the fully indicated image 22 by operating a cursor moving section 25, a mouse not shown or another device. The movement of the detailed indication cursor 23 is accompanied by the renewal of the detailed indicated image 24.

When the user employs the detailed indication cursor 23 to specify a position to carry out the calculation of the number of fragments or other calculation while watching the fully indicated image 22, the details of the specified region is shown at the detailed indicated image 24. When the selected region for calculating fragments has already been set, the region is shown as a fragment calculating mark 26 on the fully indicated image 22.

Figure 5:
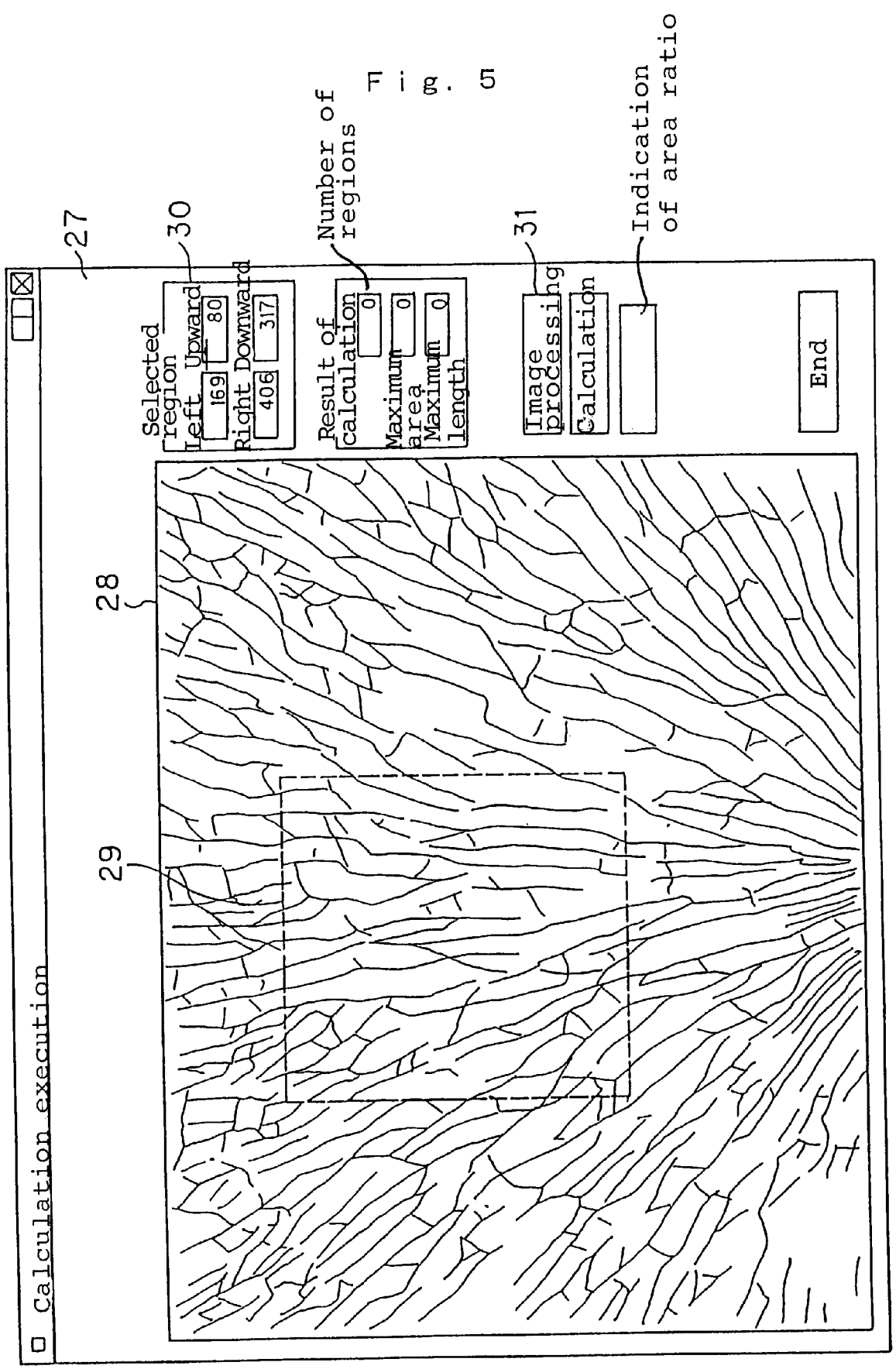
FIG. 5 is a schematic view showing a calculating operation executing screen with a tone image in a selected region to calculate the number of fragments and in surroundings of the region displayed.

Next, the calculation executing screen 27 shown in FIG. 5 is displayed on the monitor 12, and the details of the position specified by the detailed indication cursor 23 and regions around that position (for example, 160 mm×120 mm) are displayed as a calculating region tone image 28 (640×480 pixels) at a second stage of the calculating region setting function (specified positional designation). The user carries out specified positional designation of the selected region for calculating fragments, using the calculation executing screen 27. In the calculating region tone image 28, a fragment calculating region frame 29 (200×200 pixels) is displayed to show the selected region for calculating fragments (50 mm×50 mm). The fragment calculating region frame 29 can be arbitrarily moved on the calculating region tone image 28 by operating the mouse or another device, not shown. At that time, the position coordinate of the fragment calculating frame 29 is indicated at a section 30 for indicating the coordinates of a selected region. When plate glass formed in a curved shape as the test glass 3 is picked up to carry out the calculation of the number of fragments and other calculation, the size of the picked tone image or the fragment calculating region frame may be properly revised so as to be matched with the actual size when the selected region for calculating fragments is set.

When the user locates the fragment calculating region frame 29 at a desired position to designate the specified position of a selected region for calculating fragments and pushes an image processing button 31, the CPU starts performing the processing for the calculating function with respect to the selected region for calculating fragments. At that time, the positional information on the selected region for calculating fragments with respect to the entire tone image is stored on the main memory 8.

Figure 6:
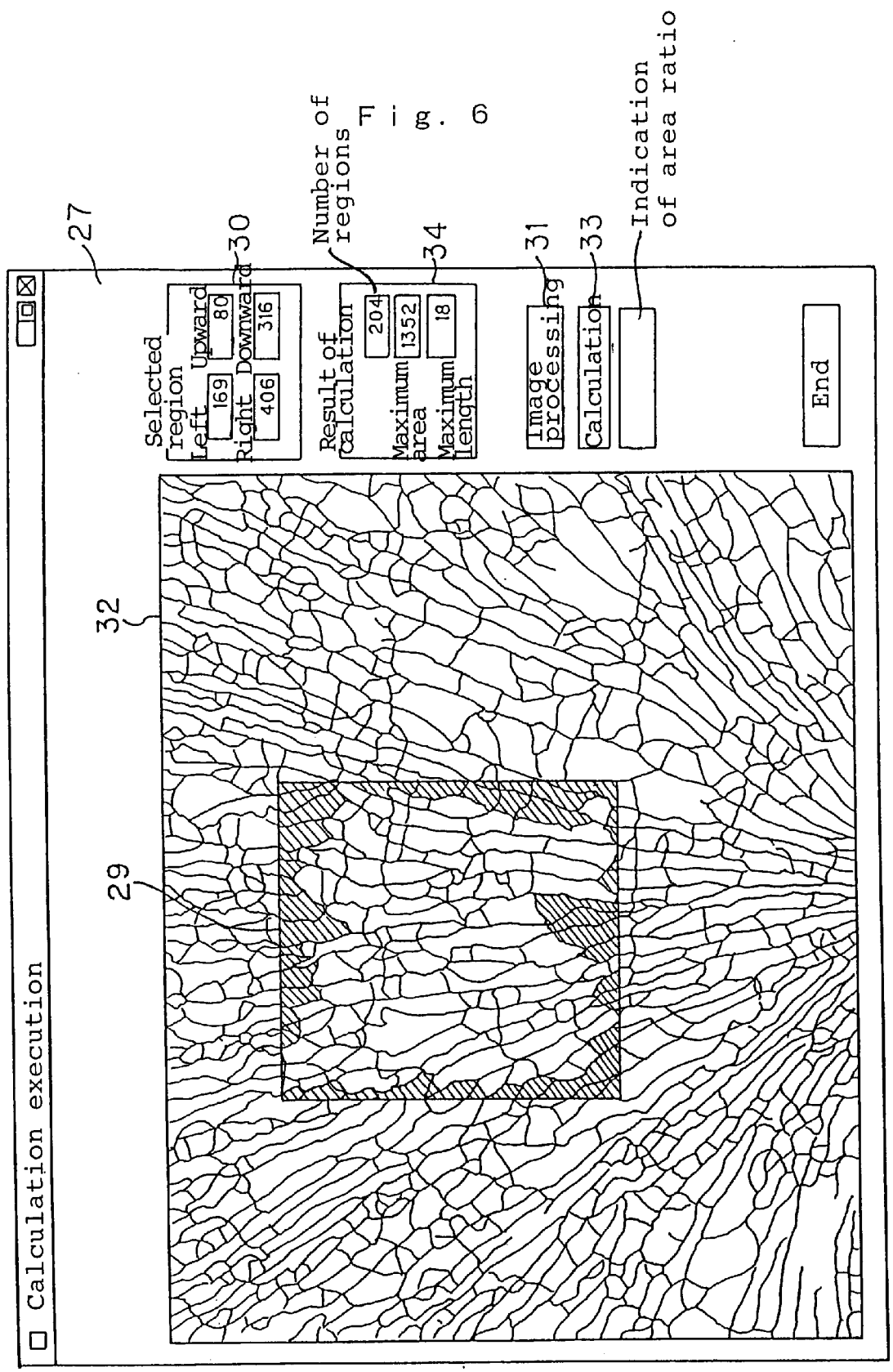
FIG. 6 is a schematic view showing a calculating operation executing screen with a binarized and noise-eliminated image in these regions displayed.

At a first stage of the calculation function, the binarization and the noise removing operation of the tone image are executed in the range of the tone image 28 in the calculating region, and a processed image 32 in the calculating region is shown on the calculation executing screen 27 as shown in FIG. 6. When the user pushes a calculating button 33, the calculation, such as calculating the numbers of fragments in the selected region, is performed, and the results of the calculation are displayed on a calculation result display section 33 as a second stage of the calculation function.

Figure 7:
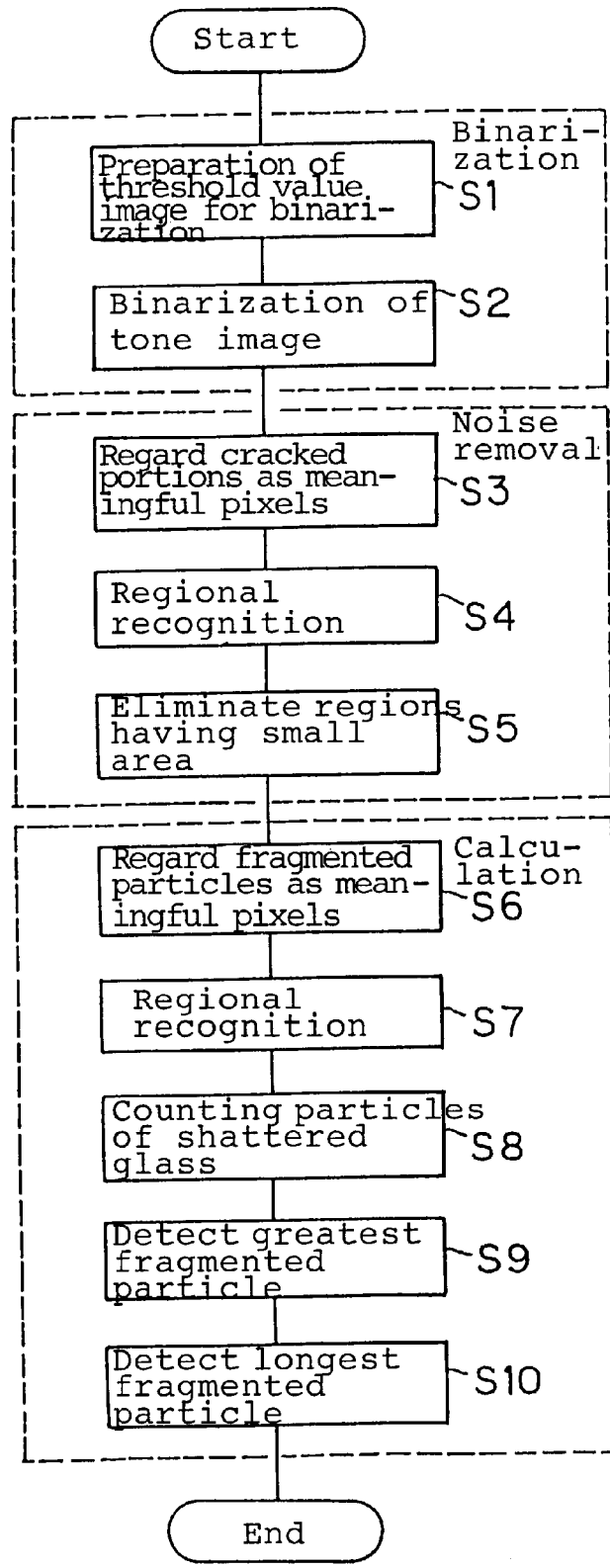
FIG. 7 is a flow chart showing processing steps with respect to a function to count the number of the fragments.

In FIG. 7 is shown a flow chart of the procedures for the calculation function. First, the tone image data in the selected region and its surrounding regions are binarized in the binarizing process. At that time, a bit-mapped image data of a threshold value image as an image representing a threshold value distribution for the binarization are prepared based on the tone image data at Step S1. After that, the tone image data are binarized according to the threshold value image at Step S2.

Figure 8:
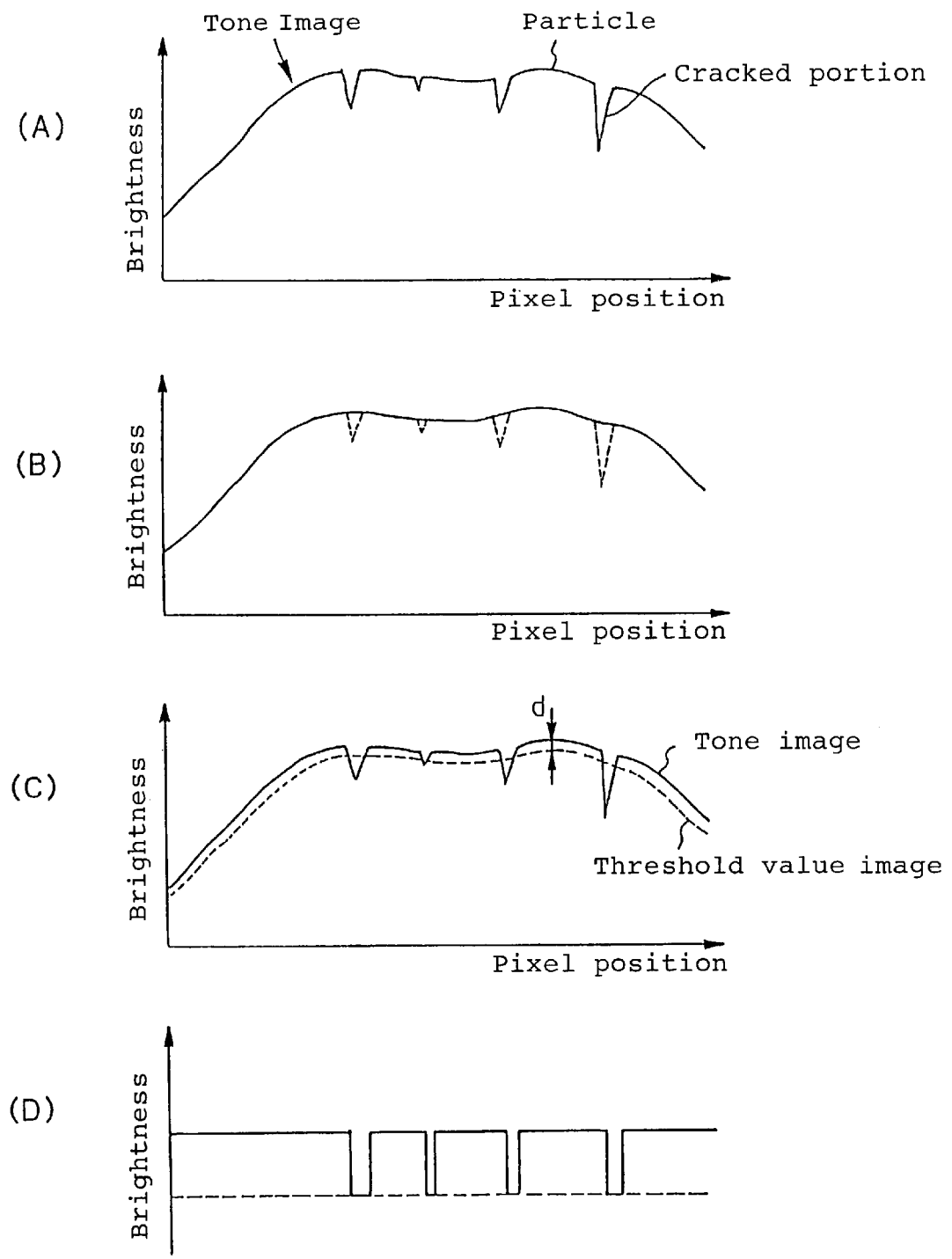
FIGS. 8(A–D) is characteristic views to explain the details of a binarizing process.

Now, the details of the binarization in this embodiment will be explained in reference to FIG. 8. The binarization aims at classifying respective pixels of the tone image into two categories. In the image processing for the fragmentation test, the binarization is performed in order to classify the tone image of fragmented test glass (hereinbelow, referred to as the fragmented glass) into portions with a crack (hereinbelow, referred to as the cracked portions) and fragmented glass portions (hereinbelow, referred to as the fragmented portions).

If an object to be classified into two categories has significantly different tone degrees in the binarization, no problems are introduced into the binarization by setting only one value as the threshold value for the binarization with respect to the entire selected region. However, the tone degrees of the cracked portions significantly vary from portions to portions in the tone image of the fragmented glass as shown in FIG. 8(A). Since it is difficult to uniformly illuminate the entire plate glass having a wide area, the tone degrees of the fragmented portions (that is to say, the background) extremely vary from positions to position in many cases. For these reasons, there is a case wherein the entire tone image cannot be properly binarized if only one threshold value for the binarization is set in the fragmentation test.

From the viewpoint that the fragmented portions have an overwhelmingly greater area than the cracked portions in the tone image of the fragmented glass, it is preferable that a noise removing filter, such as an intermediate value filter, is applied to carry out the binarization according to the brightness of the background of the tone image. In other words, the cracked portions are removed from the tone image data shown in FIG. 8(A) to perform interpolation so that a fragmented portion has a peripheral portion smoothly merged as shown in FIG. 8(B). The image data of the fragmented portion with the cracked portions removed are used as a set of threshold values for the binarization corresponding to respective pixels of the tone image of the fragmented glass, and the binarization is performed according to the brightness of the background of the tone image.

Specifically, the image data of the background indicated by a solid line in FIG. 8(B) are shifted to obtain threshold value image data. And, the tone image data indicated by the solid line are binarized by the threshold value image data indicated by a dotted line as shown in FIG. 8(C). Thus, the binarized image data can be provided as shown in FIG. 8(D). The difference d in brightness between the tone image data and the threshold value image data is set for the binarization so that the threshold value image data is smaller than the tone image data by about 1–2% if the tone image data has 256 gradations for instance.

The application of the binarization stated earlier can set an optimum threshold value for binarization to recognize the cracks in the entire tone image of the fragmented glass without failing detection according to the relatively easy procedures, and can carry out proper binarization without failure.

Figure 9:
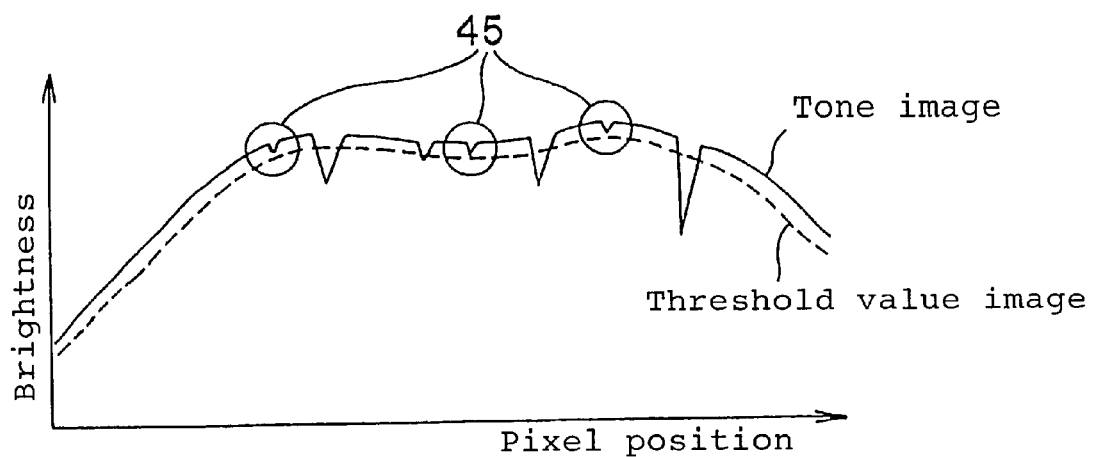
FIG. 9 is a schematic view to explain a tone distribution of portions with minute cracks formed therein.

Furthermore, a second binarization process, which will be explained herebelow may be performed in addition to the binarization stated earlier, and both binarizing processes may be used together to further improve binarization precision. Minute cracks that are formed in a substantially concentric shape with respect to the impact shock point cannot be detected even by the binarization with the threshold value image used in some cases. For example, there is a possibility that minute cracked portions 45 surrounded by circles in FIG. 9 are not detected in the binarization, and the fragments of the fragmented glass are counted at a smaller number than the actual number. If the level of the threshold value image is raised too much in order to cope with this problem of failure to detect minute cracks, noise components are increased to lower binarization precision conversely. From this viewpoint, binarization using a minute tone distribution is additionally executed, and both binarized images are combined to provide binarized image data in better fashion.

Figure 10:
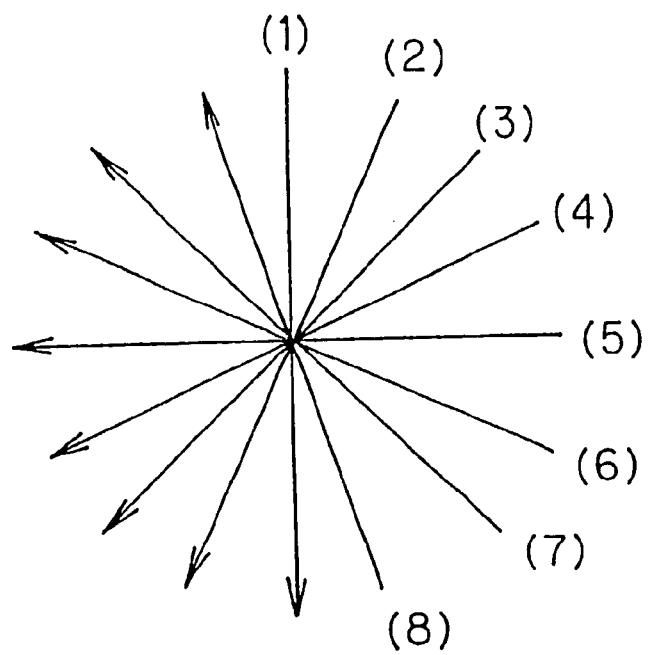
FIG. 10 is a schematic view showing tentacles for tone distribution detection.
Figure 1:
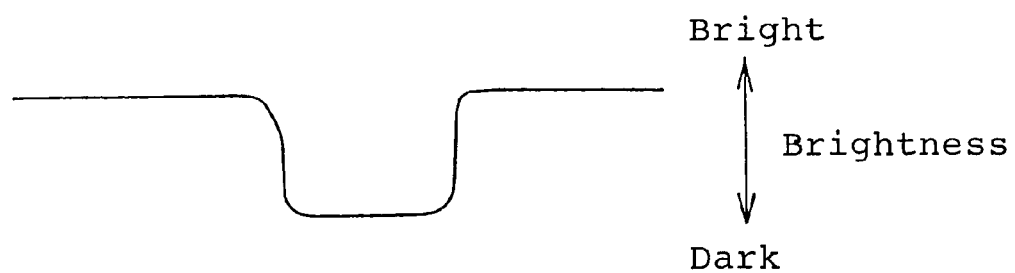

In this case, the tone distribution is first checked out about portions on (1) to (8) of tentacles in eight directions in a range including plural pixels around a noteworthy pixel as shown in FIG. 10. If in at least one of the eight directions in the tone distribution, there is a state wherein a central portion is dark and both end portions are bright as shown in FIG. 11 (a state wherein the tone distribution changes from a bright portion to a dark portion further to a bright portion), the noteworthy pixel is recognized as a pixel in a cracked portion. For example, if a difference in tone degrees due to an increase or decrease by about 1% of tone image data having 256 gradations, or 2 to 3 gradations is detected, that portion is binarized so as to be recognized as a cracked portion. After that, the binarized image data based on the threshold value image and the binarized image data based on the minute tone distribution are combined by addition. The combination of both binarized images may be carried out by calculation of logical sum, for instance, wherein if a pixel is recognized as being a cracked portion in at least one of the binarized images, the binarized image data are produced so as to recognize that pixel as being a cracked portion. By combining both binarizing operations as staged earlier, the binarization can be carried out with higher precision and in effective fashion.

Returning to FIG. 7, small cracked portions are eliminating from the binarized image data to remove noise components as the noise removing operation after the binarizing processing stated earlier. In the binarized image of the fragmented glass, the cracked portions corresponding to actual cracks have an extremely great area as the result of regional recognition since such cracked portions are continuous in a network. To the contrary, regions of the fragmented glass that have been incorrectly binarized as being cracked portions though being not cracked portions of the fragmented glass have a smaller area. The regions that have been incorrectly recognized are removed as noise components.

In this operation, cracked portions in the binarized image data are first regarded as meaningful pixels at Step S3, and regional recognition is carried out by checking out how the meaningful pixels are connected together, at Step S4. Cracked portions that have a small area among the regions regarded as cracked portions as the result of regional recognition are deleted at Step S5.

A known technique called for "labeling" wherein adjoining (coupled) meaningful pixels are labeled the same label is utilized to recognize continuous regions with the same label as one closed region.

Next, the number of the fragments, the area of the greatest fragment and the length of the longest fragment in the selected region for calculation of the fragments are detected based on the binarized image data after noise removal, as the calculating operation. In this operation, the fragmented portions in the binarized image data are first regarded as meaningful pixels at Step S6, and regional recognition is carried out by checking out how the meaningful pixels are corrected together, at Step S7. At Step S8, the number of fragments of the fragmented glass is found by counting the number of closed regions that have been regarded as fragmented portions as the result of regional recognition. A fragment that bridges the fragment calculating region frame is counted as a ½ particle. At Step S9, the area of each of the regions of the fragmented portions is calculated and the greatest fragment is detected. At Step S10, the characteristic value of shape with respect to each of the regions of fragmented portions is calculated, and the longest fragment is detected. The detection of the longest fragment is carried out by approximating the respective fragmented portions detected by the regional recognition to an ellipse and determining one with the longest major axis as the longest fragment.

When the operations for the fragment calculating function are completed, the number of the fragments in the selected region for calculating fragment (the number of the selected regions), the area of the greatest fragment (the maximum area) and the length of the fragment (the maximum length) are displayed as the result of the calculation on the calculation result displaying section 33.

After that, the positional data of the selected region for calculating fragments in the tone image, the numerical value data as the results of the calculation of fragment and other data are correlated, and these data as well as the originally picked tone image data of the fragmented glass are transmitted, as data of the test results, to a recording medium, such as the hard disk 10, to be saved. In other words, the tone image and the corresponding test results are stored on the recording media as digital data instead of the conventional blueprinted image.

In accordance with the fragmentation testing method or the fragmentation testing device according to the embodiments stated earlier, when shattered test glass is picked up, the electronic image pickup means can clearly and directly pick up cracks without failure and can provide a tone image in the substantially same level as the conventional blueprinted image, or in more effective fashion than the conventional fragmented image in sometimes.

The calculation of fragments and other operation can be accurately performed based on the picked tone image, realizing the fragmentation test so as to see whether produced plate glass meets required qualification.

In the embodiments stated earlier, after having shattered test glass, all procedures of the image pickup and the image processing except for the setting of a selected region for calculating fragments by an operator can be automatically performed to obtain data, such as the number of fragments, and the data can be saved on a recording medium as digital data of the test results. As a result, it is not necessary to manually carry out all operations, such as calculation of the number of the fragments, based on a blueprinted image of shattered test glass as in the conventional technique, and it becomes possible not only to reduce the steps of operations and labor cost but also to avoid errors by an operator. Since the test results including a tone image are saved as digital data, labor or a space required for storing a paper medium of a blueprinted image and others can be eliminated, and the cost required for storing the test results can be reduced. In addition, test results can be easily retrieved and read out later, if necessary.

INDUSTRIAL APPLICABILITY

As explained, the present invention can directly pickup an image of test glass and automatically carry out operations, such as calculation of the numbers of fragments, providing the fragmentation test with good operability and high precision.

What is claimed is:

1. A plate-shaped glass fragmentation testing method for testing a plate-shaped test glass having first and second opposite sides, comprising:

fragmenting the plate-shaped test glass;

a glass image pickup operation providing a sheet screen in substantially close contact with the second side of the plate-shaped test glass, and irradiating light for image pickup to the second side from the first side of the plate-shaped test glass, and electronically and directly picking up a projected image of the fragmented plate-shaped test glass on the screen from the second side of the plate-shaped test glass; and an image processing operation performing a calculating operation to calculate a number of fragments of the plate-shaped test glass, an area of a greatest fragment, and a length of a longest fragment in at least a selected region based on tone image signals derived from the projected image of the fragmented plate-shaped test glass.

2. The method according to claim 1, wherein in the image processing operation, the number of fragments of the plate-shaped test glass, the area of the greatest fragment, and the length of the longest fragment in at least the selected region are calculated after having classified the plate-shaped test glass into cracked portions and fragmented portions based on the tone image signals.

3. The method according to claim 1, further comprising:
a binarizing operation for binarizing the tone image signals while modifying threshold values according to brightness of a background in the tone image signals; and
wherein the calculating calculates the number of fragments of the plate-shaped test glass, the area of the greatest fragment, and the length of the longest fragment in at least a selected region based on the binarized image signals after the binarizing.

4. The method according to claim 3, wherein in the calculating, the number of fragments of the plate-shaped test glass, the area of the greatest fragment, and the length of the longest fragment in at least the selected region are calculated after having classified the plate-shaped test glass into cracked portions and fragmented portions based on the tone image signals.

5. The method according to claim 3, wherein the binarizing includes:
a first binarizing for binarizing the tone image signals into cracked portions and fragmented portions based on a threshold value image obtained by modifying the threshold values according to brightness of a background in the tone image,
a second binarizing for examining a tone distribution in a plurality of directions in a certain region around a noteworthy pixel of the tone image and for performing binarization to recognize the noteworthy pixel as a cracked portion when in at least one direction of the tone distribution a central portion is dark and both end portions are bright, and
a binarized image combining for combining the image signals binarized in the first binarizing and the image signals binarized in the second binarizing.

6. A plate-shaped glass fragmentation testing device comprising:
an image pickup unit including a light source to produce light for image pickup to irradiate a fragmented plate-shaped test glass from a first side of the plate-shaped test glass, a sheet screen provided on a second side, opposite the first side, of the plate-shaped test glass and provided in substantially close contact with the plate-shaped test glass, and an image pickup to electronically and directly pick up a projected image of the fragmented plate-shaped test glass on the screen from the second side of the plate-shaped test glass; and
an image processing unit to calculate a number of fragments of the plate-shaped test glass, an area of a greatest fragment, and a length of a longest fragment in at least a selected region based on tone image signals derived from the projected image of the fragmented plate-shaped test glass.

7. The device according to claim 6, wherein the image processing unit further calculates the number of fragments of the plate-shaped test glass, the area of a greatest fragment, and the length of a longest fragment in at least the selected region after having classified the plate-shaped test glass into cracked portions and fragmented portions based on the tone image signals.

8. The device according to claim 6, further comprising:
a binarizing means for binarizing the tone image signals of the plate-shaped test glass while modifying threshold values according to brightness of a background in the tone image; and
wherein the image processing unit further calculates the number of fragments of the plate-shaped test glass, the area of the greatest fragment, and the length of the longest fragment in at least a selected region based on the binarized image signals after the binarizing.

9. The device according to claim 8, wherein the image processing unit further calculates the number of fragments of the plate-shaped test glass, the area of the greatest fragment, and the length of the longest fragment in at least the selected region after having classified the plate-shaped test glass into cracked portions and fragmented portions based on the tone image signals.

10. A plate-shaped glass fragmentation testing method comprising:
a glass image pickup operation for electronically and directly picking up plate-shaped test glass in fragmented fashion;
a binarizing operation for binarizing tone image signals of the test glass picked up while modifying threshold values according to brightness of a background in the tone image; and
a calculating operation for calculating a number of fragments of the test glass, an area of a greatest fragment, and a length of a longest fragment in at least a selected region based on the binarized image signals after the binarizing,
wherein the binarizing operation includes a first binarizing for binarizing the tone image signals into cracked portions and fragments based on a threshold value image obtained by modifying threshold values according to the brightness of the background in the tone image, a second binarizing for examining a tone distribution in a plurality of directions in a certain region around a noteworthy pixel of the tone image and for performing binarization so as to recognize the noteworthy pixel as a cracked portion when in at least one direction of the tone distribution a central portion is dark and both end portions are bright, and a binarized image combining for combining the image signals binarized in the first binarizing and the image signals binarized in the second binarizing.

11. An image signal processing method for glass fragmentation test comprising:
inputting tone image signals obtained by picking up test glass;
binarizing the tone image signals of the test glass while modifying threshold values according to brightness of a background in the tone image; and
calculating a number of fragments of the test glass, an area of a greatest fragment, and a length of a longest fragment in at least a selected region based on the binarized image signals after the binarizing,
wherein the binarizing includes a first binarizing for binarizing the tone image signals into cracked portions and fragmented portions based on a threshold value image obtained by modifying threshold values according to the brightness of the background in the tone image, a second binarizing for examining a tone distribution in a plurality of directions in a certain region around a noteworthy pixel of the tone image and for performing binarization so as to recognize the noteworthy pixel as a cracked portion when in at least one direction of the tone distribution a central portion is dark and both end portions are bright, and a binarized combining for combining the image signals binarized in the first binarizing and the image signals binarized in the second binarizing.

* * * * *